United States Patent [19]

Andrews et al.

[11] Patent Number: 6,117,908
[45] Date of Patent: Sep. 12, 2000

[54] USE OF GABA$_B$ RECEPTOR AGONISTS AS REFLUX INHIBITORS

[75] Inventors: Paul L. R. Andrews, London, United Kingdom; Anders Lehmann, Västra Frölunda, Sweden

[73] Assignee: Astra Aktiebolag, Sodertalje, Sweden

[21] Appl. No.: 08/952,400

[22] PCT Filed: Sep. 15, 1997

[86] PCT No.: PCT/SE97/01555

§ 371 Date: Nov. 12, 1997

§ 102(e) Date: Nov. 12, 1997

[87] PCT Pub. No.: WO98/11885

PCT Pub. Date: Mar. 26, 1998

[30] Foreign Application Priority Data

Sep. 18, 1996 [SE] Sweden ................................. 9603408

[51] Int. Cl.[7] ...................... A61K 31/195; A61K 31/381; A61K 31/472; A61K 31/662
[52] U.S. Cl. ........................ 514/567; 514/114; 514/400; 514/438; 514/561; 514/562; 514/565
[58] Field of Search .................... 514/114, 400, 514/438, 567, 561, 562, 565

[56] References Cited

U.S. PATENT DOCUMENTS

| 5,036,057 | 7/1991 | Martin | 514/54 |
| 5,491,134 | 2/1996 | Sher et al. | 514/114 |

FOREIGN PATENT DOCUMENTS

| WO9009096 | 8/1990 | WIPO. |
| WO556880 | 8/1993 | WIPO. |
| WO95/29234 | 11/1995 | WIPO. |

OTHER PUBLICATIONS

Washabau et. al., Brain Research Bulletin 38: 587–594 (1995).

Nakajima et. al., Neurochem. Res. 21: 211–215 (1996).

*Primary Examiner*—Phyllis G. Spivack
*Attorney, Agent, or Firm*—White & Case LLP

[57] ABSTRACT

The present invention relates to the use of GABA$_B$ receptor agonists for the inhibition of transient lower esophageal sphincter relaxations, and for the treatment of gastro-esophageal reflux disease.

13 Claims, No Drawings

USE OF GABA_B RECEPTOR AGONISTS AS REFLUX INHIBITORS

TECHNICAL FIELD

The present invention relates to the use of $GABA_B$ receptor agonists for the inhibition of transient lower esophageal sphincter relaxations; for the treatment of gastro-esophageal reflux disease; and/or for the treatment of regurgitation in infants.

BACKGROUND ART

Reflux

In some humans, the lower esophageal sphincter (LES) is prone to relaxing more frequently than in other humans. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current therapy has aimed at reducing gastric acid secretion, or by reducing esophageal acid exposure by enhancing esophageal clearance, lower esophageal sphincter tone and gastric emptying. The major mechanism behind reflux has been considered to depend on a hypotonic lower esophageal sphincter. However, recent research (e.g. Holloway & Dent (1990) Gastroenterol. Clin. N. Amer. 19, 517–535) has shown that most reflux episodes occur during transient lower esophageal sphincter relaxations (TLESR), i.e. relaxations not triggered by swallows. It has also been shown that gastric acid secretion usually is normal in patients with GERD.

Consequently, there is a need for compounds which reduce the incidence of TLESR and thereby prevent reflux. Ideally, the compound should have an effect duration of approximately 12 h. since most reflux occurs during daytime and postprandially.

A pharmaceutical composition comprising a local anaesthetic, adapted to inhibit relaxation of the lower esophageal sphincter, is disclosed in WO 87/04077 and in U.S. Pat. No. 5,036,057.

$GABA_B$ Receptor Agonists

GABA (4-aminobutanoic acid) is an endogenous neurotransmitter in the central and peripheral nervous systems. Receptors for GABA have traditionally been divided into $GABA_A$ and $GABA_B$ receptor subtypes. $GABA_B$ receptors (for a review see Kerr, D. I. B. and Ong, J. (1995) Pharmac. Ther. vol. 67, pp.187–246) belong to the superfamily of G-protein coupled receptors. $GABA_B$ receptor agonists are described as being of use in the treatment of CNS disorders, such as muscle relaxation in spinal spasticity, cardiovascular disorders, asthma, gut motility disorders such as irritable bowel syndrome and as prokinetic and anti-tussive agents. $GABA_B$ receptor agonists have also been disclosed as useful in the treatment of emesis (WO 96/11680).

The $GABA_B$ receptor agonist baclofen (4-amino-3-(4-chlorophenyl)butanoic acid) (Swiss patent No. CH 449,046) has been the most studied of the GABA analogs.

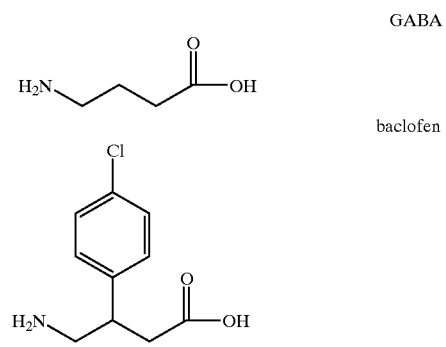

Other $GABA_B$ receptor agonists or partial agonists are disclosed in: EP 0356128; EP 0181833; EP 0399949; EP 0463969; and FR 2,722,192. For a review on the chemistry of $GABA_B$ modulators, see Froestl, W. and Mickel, S. J. in: The GABA Receptors, pp.271–296 (Eds. S. J. Enna and N. G. Bowery, Humana Press Inc., Totowa, N.J., U.S.A. 1997)

It is known in the art that drug screening can be improved by using cells which are transfected with a cloned receptor gene. Such transfected cells may offer several advantages over traditional screening, the most important being presumably selectivity. Another advantage of transfected cells is that they allow assessment of the activity of drugs on cloned human receptors. The fact that the $GABA_B$ receptor has recently been cloned (Kaupmann et al., Nature 386 (6622), 239–246, Mar. 20, 1997) thus offers the opportunity to develop more specific drugs acting on the $GABA_B$ receptor. The said article discloses two subtypes of the receptor from rat, designated $GABA_BR1a$ and $GABA_BR1b$, but it was made very clear that several other subtypes could be isolated.

DISCLOSURE OF THE INVENTION

It has been found surprisingly that $GABA_B$ receptor agonists can be used for the inhibition of transient lower esophageal sphincter relaxations, and thus for the treatment of gastro-esophageal reflux disease.

Consequently, the present invention provides the use of a $GABA_B$ receptor agonist for the manufacture of a medicament for the inhibition of transient lower esophageal sphincter relaxations (TLESR), or more specifically, for the treatment of gastroesophageal reflux disease. For the purpose of this invention, the term "agonist" should be understood as including both full agonists as well as partial agonists, whereby a "partial agonist" should be understood as a compound capable of partially, but not fully, activating the $GABA_B$ receptor.

The inhibition of TLESR also implies that the compounds can be used for the treatment of regurgitation in infants. Effective management of regurgitation in infants would be an important way of managing lung disease due to aspiration of regurgitated gastric contents, and for managing failure to thrive due to excessive loss of ingested nutrient.

In a preferred form of the invention, the $GABA_B$ receptor agonist is a substituted aminopropyl acid derivative where the acidic head is a carboxylic group, a phosphinic group, a phosphonous group or a sulfinic group.

Examples of compounds having agonistic or partially agonistic affinity to $GABA_B$ receptors and which thus can be used according to the invention are:

4-aminobutanoic acid (GABA), 4-amino-3-(4-chlorophenyl)butanoic acid (baclofen),
4-amino-3-phenylbutanoic acid,
4-amino-3-hydroxybutanoic acid,
4-amino-3-(4-chlorophenyl)-3-hydroxyphenylbutanoic acid,
4-amino-3-(thien-2-yl)butanoic acid,
4-amino-3-(5-chlorothien-2-yl)butanoic acid,
4-amino-3-(5-bromothien-2-yl)butanoic acid,
4-amino-3-(5-methylthien-2-yl)butanoic acid,
4-amino-3-(2-imidazolyl)butanoic acid,
4-guanidino-3-(4-chlorophenyl)butanoic acid,
3-amino-2-(4-chlorophenyl)-1-nitropropane,
(3-aminopropyl)phosphonous acid,
(4-aminobut-2-yl)phosphonous acid,
(3-amino-2-methylpropyl)phosphonous acid,
(3-aminobutyl)phosphonous acid,
(3-amino-2-(4-chlorophenyl)propyl)phosphonous acid,
(3-amino-2-(4-chlorophenyl)-2-hydroxypropyl)phosphonous acid,
(3-amino-2-(4-fluorophenyl)propyl)phosphonous acid,
(3-amino-2-phenylpropyl)phosphonous acid,
(3-amino-2-hydroxypropyl)phosphonous acid,
(E)-(3-aminopropen-1-yl)phosphonous acid,
(3-amino-2-cyclohexylpropyl)phosphonous acid,
(3-amino-2-benzylpropyl)phosphonous acid,
[3-amino-2-(4-methylphenyl)propyl]phosphonous acid,
[3-amino-2-(4-trifluoromethylphenyl)propyl]phosphonous acid,
[3-amino-2-(4-methoxyphenyl)propyl]phosphonous acid,
[3-amino-2-(4-chlorophenyl)-2-hydroxypropyl]phosphonous acid,
(3-aminopropyl)methylphosphinic acid,
(3-amino-2-hydroxypropyl)methylphosphinic acid,
(3-aminopropyl)(difluoromethyl)phosphinic acid,
(4-aminobut-2-yl)methylphosphinic acid,
(3-amino-1-hydroxypropyl)methylphosphinic acid,
(3-amino-2-hydroxypropyl)(difluoromethyl)phosphinic acid,
(E)-(3-aminopropen-1-yl)methylphosphinic acid,
(3-amino-2-oxo-propyl)methyl phosphinic acid,
(3-aminopropyl)hydroxymethylphosphinic acid,
(5-aminopent-3-yl)methylphosphinic acid,
(4-amino-1,1,1-trifluorobut-2-yl)methylphosphinic acid,
(3-amino-2-(4-chlorophenyl)propyl)sulfinic acid,
3-aminopropylsulfinic acid.

Preferably, the compound having agonistic or partially agonistic affinity to a GABA$_B$ receptor is any one of the following compounds:
4-amino-3-(4-chlorophenyl)butanoic acid (baclofen),
(3-aminopropyl)methylphosphinic acid,
(3-amino-2-hydroxypropyl)methylphosphinic acid,
4-aminobutanoic acid (GABA),
(3-amino-2-(4-chlorophenyl)propyl)sulfinic acid,
(3-aminopropyl)(difluoromethyl)phosphinic acid,
(3-amino-2-oxo-propyl)methyl phosphinic acid,
4-amino-3-(5-chlorothien-2-yl)butanoic acid,
(3-aminopropyl)phosphonous acid.

The use of pharmaceutically acceptable salts of GABA$_B$ ligands for the disclosed purposes is also included in the invention. Most known GABA$_B$ ligands such as for example baclofen, (3-aminopropyl) methylphosphinic acid and (3-amino-2-(S)-hydroxypropyl)-methylphosphinic acid are of amphoteric nature and may be present in the form of internal salts. They also can form acid addition salts and salts with bases. Such salts are particularly pharmaceutically acceptable acid addition salts, as well as pharmaceutically acceptable salts formed with bases. Suitable acids for the formation of such salts include, for example, mineral acids such as hydrochloric, hydrobromic, sulfuric or phosphoric acid or organic acids such as organic sulfonic acids and organic carboxylic acids. Salts of GABA$_B$ ligands with bases are, for example, alkali metal salts, e.g. sodium or potassium salts, or alkaline earth metal salts, e.g. calcium or magnesium salts as well as ammonium salts, such as those with ammonia or organic amines.

The use of optical isomers of GABA$_B$ ligands for the disclosed purposes is also included in the invention. Many known GABA$_B$ ligands such as for example baclofen and (3-amino-2-(S)-hydroxypropyl)methylphosphinic acid are chiral compounds due to the presence of an asymmetric carbon atom. Depending on the presence of asymmetric atoms, the GABA$_B$ ligands may be in the form of mixtures of isomers, particularly racemates, or in the form of pure isomers, especially enantiomers.

In another aspect, the invention provides a method for the inhibition of transient lower esophageal sphincter relaxations which comprises administration to a mammal, including man, in need of such treatment an effective amount of a GABA$_B$ receptor agonist as defined above.

Included in the invention is also a pharmaceutical composition for use in the inhibition of transient lower esophageal sphincter relaxations. More specifically, the pharmaceutical composition is useful for the treatment of gastroesophageal reflux disease and/or for treatment of regurgitation in infants. The active ingredient in the pharmaceutical composition can be any one of the GABA$_B$ receptor agonists as defined above.

Daily Dose

For use as an inhibitor of TLESR and as a reflux inhibitor, the GABA$_B$ receptor agonist may be used at doses appropriate for other conditions for which GABA$_B$ receptor agonists are known to be useful. The typical daily dose of the active substance varies within a wide range and will depend on various factors such as for example the individual requirement of each patient and the route of administration. In general, dosages will be in the range of 1 μg to 100 mg per day and kg body weight, preferably 10 μg to 10 mg per day and kg body weight.

Pharmaceutical Formulations

For clinical use, the compounds of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.2–20% by weight in preparations for parenteral use and preferably between 1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention. vegetable oil, fat, or other suitable vehicle for soft gelatin capsules. Hard gelatin capsules may contain granules of the active compound. Hard gelatin capsules may also contain the active compound in combination with solid powdered ingredients such as lactose, saccharose, sorbitol, mannitol, potato starch, corn starch, arnylopectin, cellulose derivatives or gelatin.

Dosage units for rectal administration may be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharin and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

Screening for Compounds Active Against TLESR

Further included in the invention is the use of cells, transfected with a nucleotide sequence encoding a $GABA_B$ receptor, for screening purposes, in order to identify inhibitors of transient lower esophageal sphincter relaxations. The $GABA_B$ receptor may be any one of the $GABA_B$ receptor subtype genes, such as $GABA_BR1a$ or the $GABA_BR1b$ or the hitherto uncloned subtypes of the $GABA_B$ receptor. The nucleotide sequences may be derived from any species, but preferably from a mammal and most preferably from man.

Consequently, the invention further provides a method for the screening of compounds which are inhibitors of transient lower esophageal sphincter relaxations, comprising the use of a nucleotide sequence encoding a $GABA_B$ receptor. In a preferred form such a method comprises the steps (a) transfecting a cultured cell with a nucleotide sequence encoding a $GABA_B$ receptor, so that a $GABA_B$ receptor is expressed on the surface of the cell; (b) contacting a test compound with the cell; and (c) determining whether the test compound binds to, and/or activates, the $GABA_B$ receptor. The $GABA_B$ receptor can e.g. be $GABA_BR1a$ or $GABA_BR1b$.

EXAMPLES

Materials and Methods

Adult Labrador retriever dogs of both sexes (5 males, 3 females) weighing 20–30 kg were used. A cervical esophagostomy was formed to allow intubation. After a recovery period, the dogs were used in control experiments until a stable and reliable control response had been achieved. The dogs were used in other experiments before they were given the $GABA_B$ receptor agonists, but they were always allowed a wash-out period of at least two days during which time no drugs were administered. Every fourth experiment on each dog was a control experiment to ensure stability and reproducibility of the results.

The experiments were started at about 8 a.m. at which time the animals had been fasting for approximately 17 hrs. The dog was placed in a Pavlov stand to which it had been accustomed previously. A thin silicone catheter with a distal opening was introduced retrogradely through the esophagostomy into the pharynx to record swallowing. The catheter was perfused with air at approximately 2 ml/min. A multilumen assembly was positioned so that pressures could be recorded in the proximal stomach, LES and at four sites in the distal esophagus. The assembly was fitted with a 6 cm long sleeve to measure LES pressure reliably. Gastric and LES channels were perfused with distilled degassed water at 0.45 ml/min and esophageal channels at 0.1 ml/min. A low-compliance pneumohydraulic pump was used to achieve optimal perfusion conditions. Intraluminal pressures were measured with external pressure transducers. The signals were amplified and acquired using LabWindows/CVI software (version 3.1). Pressure calibrations were done at 0 and 100 mm Hg with the multilumen assemblies placed at a level slightly below the pressure transducers. The dog was positioned so that the average intragastric (i.g.) pressure approximated 0 mm Hg. An antimony pH-electrode was positioned 3 cm orad to the upper margin of the LES, and the signals were acquired as described above. Analysis of acquired signals was made using LabWindows software.

Baseline measurement was done for at least 10 min, and then vehicle (0.9% NaCl; 0.5 ml/kg) or a $GABA_B$ receptor agonist was given i.v. over 2 min. Ten min after the completion of the administration, nutrient was infused i.g. via the multilumen assembly at a rate of 100 ml/min (30 ml/kg). GABA was given as a continuous i.v. infusion which commenced 10 min before nutrient administration; and R, S,-baclofen was in some cases given intragastrically 30 min before nutrient. The nutrient contained 10% peptone (w/v), 5% Intralipid (v/v) and 5% D-glucose (w/v) and was acidified to pH 3.0 with HCl. Immediately after the infusion, air was insufflated at 40 ml/min to make up a total time of 90 min starting from the commencement of nutrient infusion. The dog was then extubated and a baseline measurement was done to ensure that no drift had occurred.

A TLESR was identified by the following criteria; The difference between LES and i.g. pressures was less than 2 mm Hg, the duration was more than 0.5 s and the relaxation was not triggered by primary peristalsis (i.e. by a pharyngeal signal). The rate of pressure drop was more than 10 mm Hg/s. Most, but not all, TLESR could also be detected aurally by a characteristic noise at the esophagostomy (i.e. belching). The total number of TLESR was calculated for the first 45 min period and entire experiment (90 min). The effect of $GABA_B$ receptor agonists was expressed relative to individual control data (n≧5). Each agonist was tested in at least two different dogs.

Results and Discussion

TLESR virtually never occurred in the fasting state but always after nutrient infusion and air insufflation. The incidence of TLESR varied significantly between dogs but the intraindividual variation was low.

$GABA_B$ receptor agonists dose-dependently reduced the incidence of TLESR. The inhibition at 45 min was greater than that calculated for the entire experimental period (90 min). Since distension of the stomach is the chief stimulus for TLESR, the 45 min value is clearly the most relevant measure when inhibiting compounds are administered: A reduction in TLESR leads to an enhanced gas-induced gastric distension and consequently to a new threshold. This confounding effect is less pronounced at the beginning of the experiment (see below).

The inhibitory effect of $GABA_B$ receptor agonists on TLESR was noted in the absence of behavioural side effects with the exception of the high R,S-baclofen dose which induced some sedation that disappeared approximately one hour after the administration.

In control experiments, the i.g. pressure increased from 0 to about 4 mm Hg during nutrient infusion/air insufflation. Doses of $GABA_B$ receptor agonists that afforded an almost complete inhibition of TLESR were accompanied by larger increments in i.g. pressure (10–13 mm Hg). Such high i.g pressures occasionally produced emesis at the end of the experiment. They result from the inability of the dogs to vent gas from the stomach when TLESR are abolished.

The results (Table 1) indicate that $GABA_B$ receptor agonists inhibit the occurrence of TLESR after a liquid meal followed by air insufflation. The effect is not secondary to sedation or somnolence. It is concluded that compounds having affinity to $GABA_B$ receptors may be useful therapeutic agents in the treatment of gastroesophageal reflux disease.

TABLE 1

Effect of various $GABA_B$ receptor agonists on TLESR in dog (mean ± SEM). All compounds were given intravenously unless it is stated otherwise.

| Compound | Dose (mg/kg) | % of control at 45 min | % of control at 90 min |
|---|---|---|---|
| R, S-baclofen | 0.3 | 47 ± 6 | 66 ± 8 |
|  | 1.5 | 11 ± 6 | 43 ± 19 |
| R, S-baclofen (intragastric admin.) | 1.5 | 12 ± 6 | 54 ± 12 |
| R-baclofen | 0.3 | 36 ± 10 | 40 ± 11 |
| S-baclofen | 1.5 | 76 ± 10 | 92 ± 10 |
| (3-aminopropyl) methylphosphinic acid | 0.003 | 57 ± 12 | 76 ± 5 |
|  | 0.01 | 32 ± 8 | 39 ± 7 |
|  | 0.03 | 25 ± 4 | 50 ± 17 |
|  | 0.1 | 5 ± 5 | 33 ± 9 |
| (3-Amino-2(S)-hydroxypropyl)methylphosphinic acid | 0.03 | 53 ± 7 | 65 ± 10 |
|  | 0.3 | 0 ± 0 | 38 ± 6 |
| GABA | 1.8[1] | 62 ± 2 | 61 ± 3 |
|  | 5.4[1] | 57 ± 6 | 54 ± 10 |

[1]Given as intravenous infusion over 100 min, i.e. 10 min before and during nutrient and air stimulation.

What is claimed is:

1. A method for the inhibition of transient lower esophageal sphincter relaxations which comprises administering to a mammal in need of such treatment an effective amount of a $GABA_B$ receptor agonist, or a pharmaceutically acceptable salt or an optical isomer of the $GABA_B$ receptor agonist.

2. The method according to claim 1 for the treatment of gastroesophageal reflux disease.

3. The method according to claim 1 for the treatment of regurgitation in infants.

4. The method according to any one of claims 1 to 3 wherein the $GABA_B$ receptor agonist is a substituted aminopropyl acid derivative selected from 4-aminobutanoic acid (GABA),
4-amino-3-(4-chlorophenyl)butanoic acid (baclofen),
4-amino-3-phenylbutanoic acid,
4-amino-3-hydroxybutanoic acid,
4-amino-3-(4-chlorophenyl)-3-hydroxyphenylbutanoic acid,
4-amino-3-(thien-2-yl)butanoic acid,
4-amino-3-(5-chlorothien-2-yl)butanoic acid,
4-amino-3-(5-bromothien-2-yl)butanoic acid,
4-amino-3-(5-methylthien-2-yl)butanoic acid,
4-amino-3-(2-imidazolyl)butanoic acid,
4-guanidino-3-(4-chlorophenyl)butanoic acid,
(3-aminopropyl)phosphonous acid,
(4-aminobut-2-yl)phosphonous acid,
(3-amino-2-methylpropyl)phosphonous acid,
(3-aminobutyl)phosphonous acid,
(3-amino-2-(4-chlorophenyl)propyl)phosphonous acid,
(3-amino-2-(4-chlorophenyl)-2-hydroxypropyl) phosphonous acid,
(3-amino-2-(4-fluorophenyl)propyl)phosphonous acid,
(3-amino-2-phenylpropyl)phosphonous acid,
(3-amino-2-hydroxypropyl)phosphonous acid,
(E)-(3-aminopropen-1-yl)phosphonous acid,
(3-amino-2-cyclohexylpropyl)phosphonous acid,
(3-amino-2-benzylpropyl)phosphonous acid,
[3-amino-2-(4-methylphenyl)propyl]phosphonous acid,
[3-amino-2-(4-trifluoromethylphenyl)propyl] phosphonous acid,
[3-amino-2-(4-methoxyphenyl)propyl]phosphonous acid,
[3-amino-2-(4-chlorophenyl)-2-hydroxypropyl] phosphonous acid,
(3-aminopropyl)methylphosphinic acid,
(3-amino-2-hydroxypropyl)methylphosphinic acid,
(3-aminopropyl)(difluoromethyl)phosphinic acid,
(4-aminobut-2-yl)methylphosphinic acid,
(3-amino-1-hydroxypropyl)methylphosphinic acid,
(3-amino-2-hydroxyropyl)(difluoromethyl)phosphinic acid,
(E)-(3-aminopropen-1-yl)methylphosphinic acid,
(3-amino-2-oxo-propyl)methylphosphinic acid,
(3-aminopropyl)hydroxymethylphosphinic acid,
(5-aminopent-3-yl)methylphosphinic acid,
(4-amino-1,1,1-trifluorobut-2-yl)methylphosphinic acid,
(3-amino-2-(4-chlorophenyl)propyl)sulfinic acid, and
3-aminopropylsulfinic acid.

5. The method according to claim 4 wherein the $GABA_B$ receptor agonist is 4-amino-3-(4-chlorophenyl)butanoic acid (baclofen).

6. The method according to claim 4 wherein the $GABA_B$ receptor agonist is (3-aminopropyl)methylphosphinic acid.

7. The method according to claim 4 wherein the $GABA_B$ receptor agonist is (3-amino-2-hydroxypropyl) methylphosphinic acid.

8. The method according to claim 4 wherein the $GABA_B$ receptor agonist is 4-aminobutanoic acid (GABA).

9. The method according to claim 4 wherein the $GABA_B$ receptor agonist is (3-amino-2-(4-chlorophenyl)propyl) sulfinic acid.

10. The method according to claim 4 wherein the $GABA_B$ receptor agonist is (3-aminopropyl)(difluoromethyl) phosphinic acid.

11. The method according to claim 4 wherein the $GABA_B$ receptor agonist is (3-amino-2-oxo-propyl) methylphosphinic acid.

12. The method according to claim 4 wherein the $GABA_B$ receptor agonist is 4-amino-3-(5-chlorothien-2-yl)butanoic acid.

13. The method according to claim 4 wherein the $GABA_B$ receptor agonist is (3-aminopropyl)phosphonous acid.

* * * * *